United States Patent [19]
Powles et al.

[11] Patent Number: 5,645,537
[45] Date of Patent: Jul. 8, 1997

[54] ASPIRATION NEEDLE AND SYRINGE FOR USE THEREWITH, APPARATUS INCORPORATING THE SAME AND KIT FOR USE IN FINE NEEDLE ASPIRATION CYTOLOGY, AND METHOD

[75] Inventors: Trevor J. Powles, Chipstead Surrey, United Kingdom; Mir A. Imran, Palo Alto, Calif.

[73] Assignee: Advanced Cytometrix, Inc., Sunnyvale, Calif.

[21] Appl. No.: 228,551

[22] Filed: Apr. 15, 1994

Related U.S. Application Data

[63] Continuation-in-part of Ser. No. 49,998, Apr. 20, 1993, Pat. No. 5,330,443.

[51] Int. Cl.$^6$ .................. A61M 5/00; A61M 5/31
[52] U.S. Cl. .................. 604/240; 604/35; 604/272; 128/752
[58] Field of Search .................. 604/140, 141, 604/149, 151, 156, 28, 35, 240, 272, 119; 128/749, 752–755, 763

[56] References Cited

U.S. PATENT DOCUMENTS

| | | | |
|---|---|---|---|
| 2,918,917 | 12/1959 | Emerson | 601/41 X |
| 4,338,932 | 7/1982 | Georgi et al. | 604/28 |
| 4,391,274 | 7/1983 | Kagan | 604/190 |
| 4,401,124 | 8/1983 | Guess et al. . | |
| 4,504,264 | 3/1985 | Kelman | 604/22 |
| 4,581,024 | 4/1986 | Swenson | 604/240 |
| 4,582,061 | 4/1986 | Fry . | |
| 4,605,011 | 8/1986 | Naslund | 128/752 |
| 4,834,722 | 5/1989 | Zenz | 604/272 |
| 4,838,281 | 6/1989 | Rogers et al. | 128/752 |
| 4,989,614 | 2/1991 | Dejter, Jr. et al. | 128/752 |
| 5,017,919 | 5/1991 | Yamada et al. | 604/243 |
| 5,018,530 | 5/1991 | Rank et al. | 128/749 |
| 5,045,053 | 9/1991 | Kothe | 604/21 |
| 5,217,438 | 6/1993 | Davis et al. | 604/198 |
| 5,254,085 | 10/1993 | Cleveland, Jr. | 604/35 |
| 5,282,476 | 2/1994 | Terwilliger | 128/753 |
| 5,318,014 | 6/1994 | Carter | 601/2 |
| 5,330,443 | 7/1994 | Powles et al. | 604/240 |
| 5,492,130 | 2/1996 | Chiou | 128/753 |

FOREIGN PATENT DOCUMENTS

| | | | |
|---|---|---|---|
| 2632190 | 12/1989 | France | 604/110 |
| 0706150 | 3/1954 | United Kingdom . | |
| 2018231 | 2/1982 | United Kingdom . | |

OTHER PUBLICATIONS

INRAD OmniKit package insert for "Quad Pass General Site Aspiration Biopsy Kit" Copyright 1991, DLP, Inc.

*Primary Examiner*—Corrine M. McDermott
*Assistant Examiner*—V. Alexander
*Attorney, Agent, or Firm*—Flehr, Hohbch, Test, Albritton & Herbert

[57] ABSTRACT

An aspiration needle for use with a syringe for fine needle aspiration cytology comprising a rigid elongate tubular member having distal and proximal extremities. The distal extremity is formed to provide a sharp point. The tubular member has a bore extending therethrough from the distal extremity to the proximal extremity. A body is secured to the proximal extremity of the tubular member and forms a chamber therein in communication with the bore of the tubular member. The chamber is formed by a sloping uninterrupted side wall leading to the bore of the tubular member. The body includes a fitting for receiving the syringe and for establishing communication between the syringe and the chamber.

4 Claims, 4 Drawing Sheets

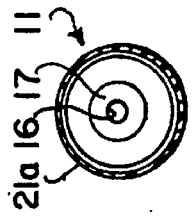
FIG.2
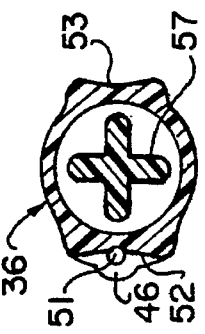
FIG.4
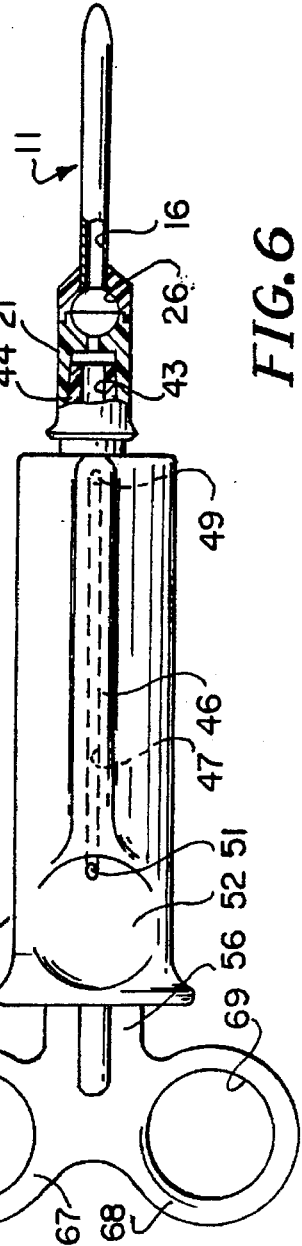
FIG.5
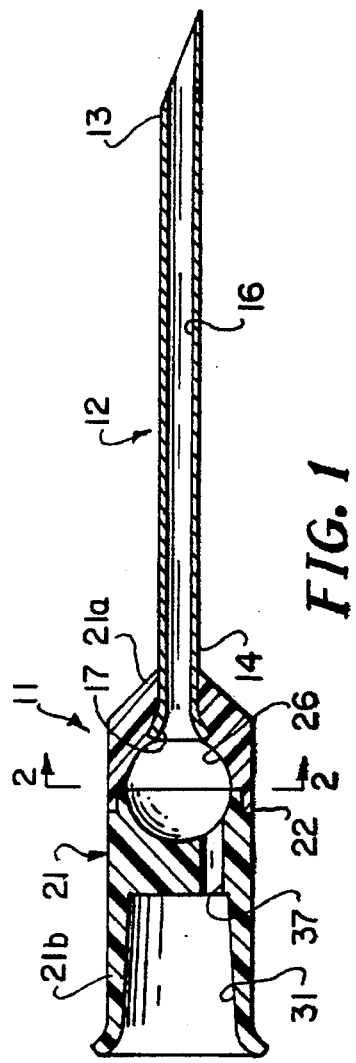
FIG.1
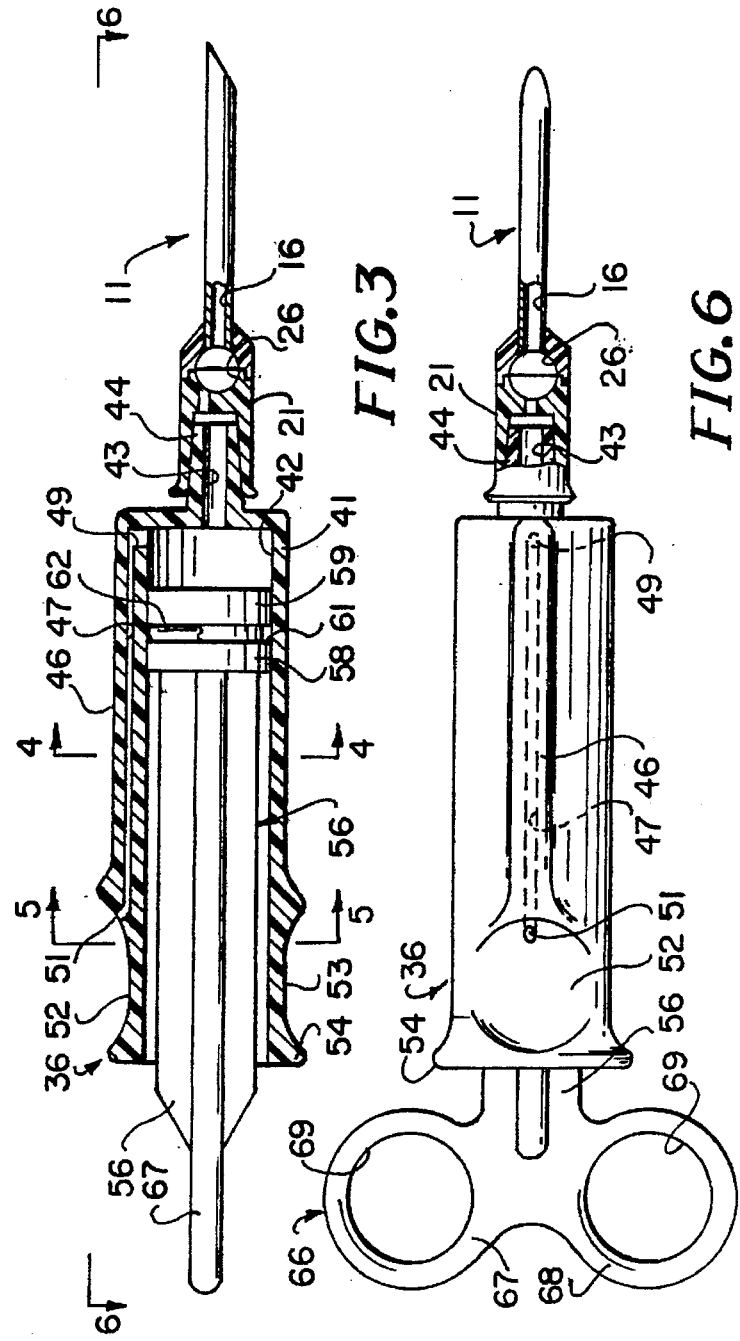
FIG.3
FIG.6

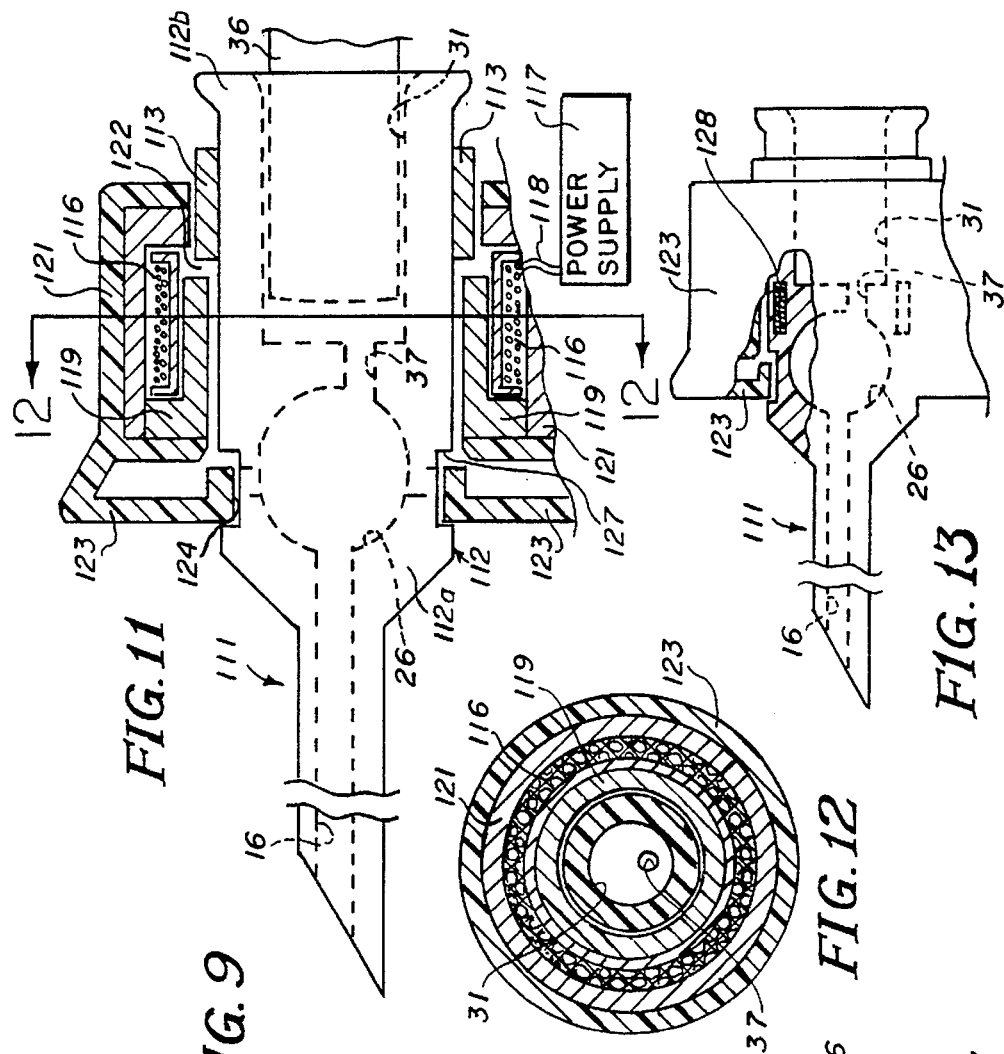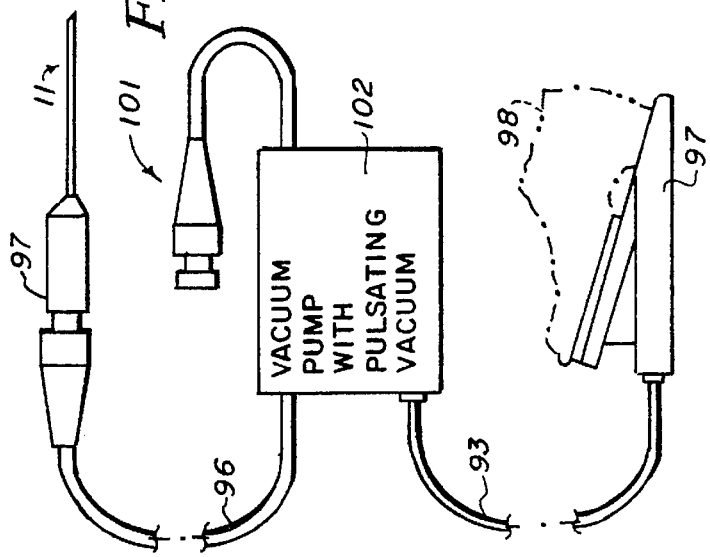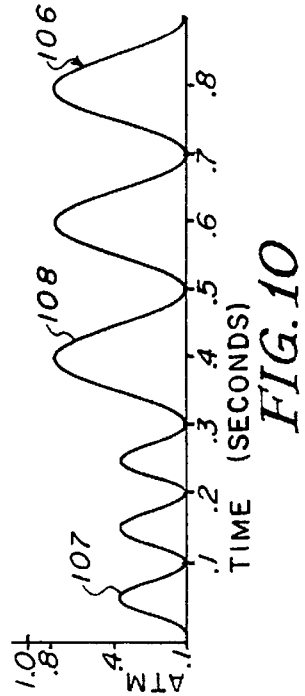

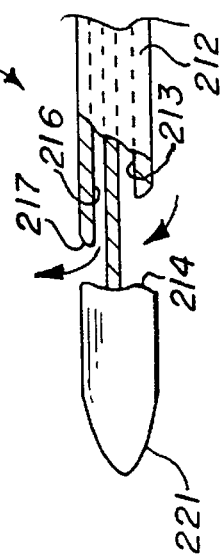
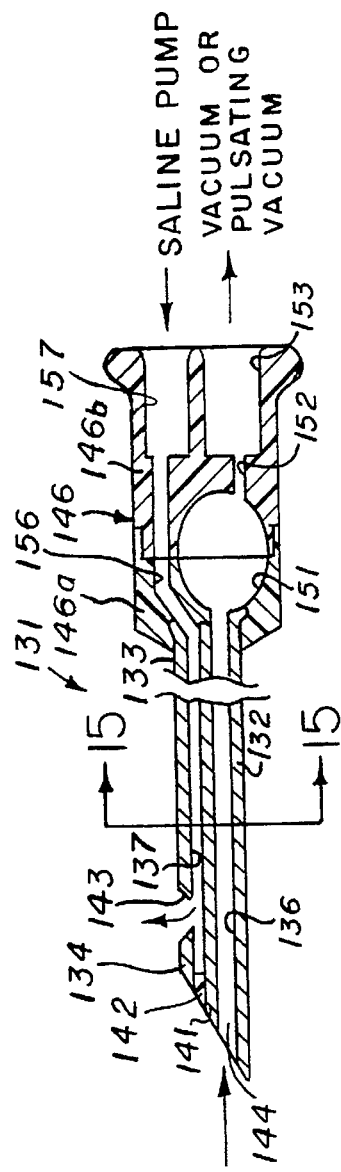
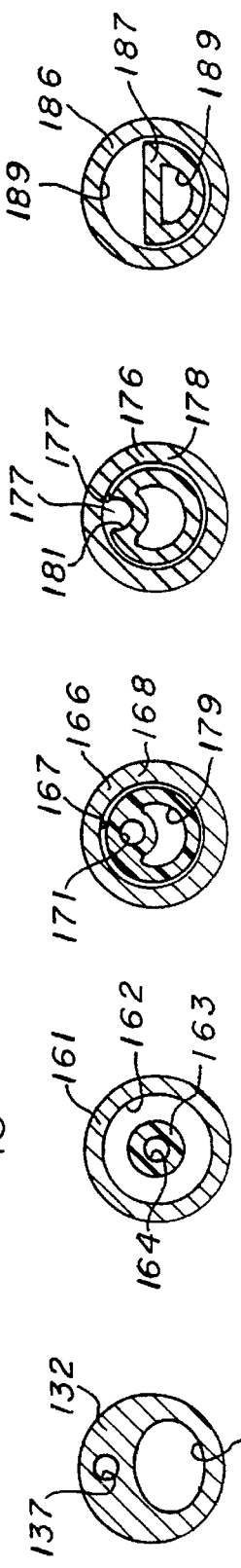
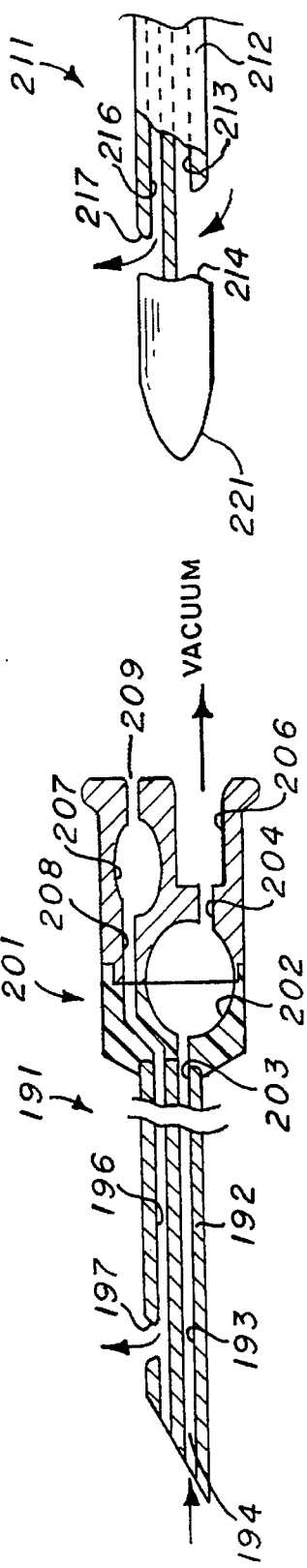

ASPIRATION NEEDLE AND SYRINGE FOR USE THEREWITH, APPARATUS INCORPORATING THE SAME AND KIT FOR USE IN FINE NEEDLE ASPIRATION CYTOLOGY, AND METHOD

This application is a continuation-in-part of application Ser. No. 08/049,998 filed on Apr. 20, 1993 now U.S. Pat. No. 5,330,443.

This invention relates to an aspiration needle, a syringe for use therewith, apparatus incorporating the same and kit for use in fine needle aspiration cytology.

Fine needle aspiration cytology has heretofore been utilized as a standard technique for the diagnosis of cancer utilizing a standard 23 gauge intravenous needle attached to a standard 10 milliliter syringe. In such a technique, the intravenous needle is passed through the skin into the tumor. The barrel of the syringe is withdrawn 3 or 4 milliliters while attached to the needle as the needle is passed three or four times through the tumor. This procedure sucks up a small amount of tissue fluid together with loose cells into the needle with some concurrent spillage up into the nozzle of the syringe. The needle is then removed from the tumor and detached from the syringe. Air is then drawn up into the syringe. The needle is reattached and the small amount of fluid with cells therein in the needle is forced out of the needle by operation of the syringe and blown onto a microscopic slide. The small amount of fluid is then smeared against another slide to produce a film on both slides which is then air dried and appropriately stained. Typically an accurate analysis of the lump can be made from a microscopic examination of these slides by an expert. In such a procedure it has been found that with a standard 23 gauge needle, the volume of the needle is often exceeded by the aspirate so that the sample passes up into the socket of the needle connected to the syringe and is partly entrapped therein preventing expression of the sample onto the slide. Also, it has been found that in many cases, the sample so obtained is inadequate to provide a clear diagnosis. Furthermore, newly developed immunocytochemical techniques for detecting proteins in cells can be used on cytological preparations for predicting growth characteristics, prognosis and likely response to treatment. These techniques require larger numbers of cells, than are currently obtained using standard aspiration equipment. Utilizing such standard intravenous needles, it has only been possible to obtain something in the order of 5,000-10,000 cells which is only adequate for cytodiagnosis in about 60-70% of the patients. There is therefore need for a new and improved aspiration needle which will make it possible to obtain larger cell samples without increasing the external size of the needle. In addition, it has been found that the syringes utilized with such aspiration needles have been difficult to use during such aspiration procedures. There is therefore also a need for a new and improved syringe for use with the improved aspiration needle.

In general, it is an object of the present invention to provide an aspiration needle, a syringe for use therewith, an apparatus incorporating the same and a kit for use in fine needle aspiration cytology.

Another object of the invention is to provide an aspiration needle of the above character in which larger cell samples can be obtained without increasing the outside diameter of the needle.

Another object of the invention is to provide an aspiration needle of the above character in which smooth polished surfaces are provided within the needle to minimize cell damage.

Another object of the invention is to provide an aspiration needle of the above character in which aspirated cells do not become entrapped in the aspiration needle.

Another object of the invention is to provide an aspiration needle of the above character which is made in a small size so as to cause as little discomfort as possible to the patient.

Another object of the invention is to provide an aspiration needle of the above character which is sized so as to minimize bleeding and damage around the tumor and to inhibit disturbing the integrity of the tumor.

Another object of the invention is to provide an aspiration needle of the above character which has the necessary column strength to penetrate skin soft tissues and the tumor.

Another object of the invention is to provide an aspiration needle of the above character which can be readily manufactured.

Another object of the invention is to provide an aspiration needle of the above character to provide larger cell samples for preparing adequate cell suspensions for use in immunocytochemical techniques.

Another object of the invention is to provide a syringe which can be utilized with the aspiration needle which is easy to operate.

Another object of the invention is to provide a syringe of the above character in which air can be introduced into the syringe without removing the syringe from the aspiration needle.

Another object of the invention is to provide an apparatus of the above character in which the vacuum for the aspiration needle is provided by a foot operated mechanism.

Another object of the invention is to provide an aspiration needle of the above character in which a pulsating vacuum is utilized to create mechanical motion of the cells.

Another object of the invention is to provide an apparatus of the above character in which the aspiration needle is mechanically vibrated.

Another object of the invention is to provide an aspiration needle of the above character in which a dual lumen is provided in the needle, one for introducing a fluid, as for example a saline solution through one of lumens, and the other for creating a vacuum.

Another object of the invention is to provide a kit which includes a aspiration needle, a syringe for use therewith and a sealed sterile vial containing a chemically defined medium so that the kit provides all that is required for a cancer screening operation using fine needle aspiration cytology.

Additional objects and features of the invention will appear from the following description in which the preferred embodiments are set forth in detail in conjunction with the accompanying drawings.

FIG. 1 is a side-elevational view in cross section of an aspiration needle incorporating the present invention.

FIG. 2 is a cross-sectional view taken along the line 2—2 of FIG. 1.

FIG. 3 is a side-elevational view in cross section of a syringe incorporating the present invention mounted on the aspiration needle shown in FIG. 1.

FIG. 4 is a cross-sectional view taken along the line 4—4 of FIG. 3.

FIG. 5 is a cross-sectional view taken along the line 5—5 of FIG. 3.

FIG. 6 is a side-elevational view taken along the line 6—6 of FIG. 3.

FIG. 9 is a schematic illustration of another embodiment of a foot-operated apparatus incorporating the present invention for use in fine needle aspiration cytology utilizing a pulsating vacuum.

FIG. 10 is a graph showing the amplitude and frequency of the pulsating vacuum utilized in the embodiment of the invention shown in FIG. 9.

FIG. 11 is another embodiment of the apparatus incorporating the present invention in which mechanical means is provided for vibrating the needle.

FIG. 12 is a cross-sectional view taken along the line 12—12 of FIG. 11.

FIG. 13 is a side-elevational view showing another embodiment of the apparatus shown in FIG. 11 for mechanically vibrating the aspiration needle.

FIG. 14 is a side elevational view in cross-section of another embodiment of an aspiration needle incorporating the present invention having dual lumens therein.

FIG. 15 is a cross-sectional view taken along the line 15—15 of FIG. 14.

FIGS. 15A, 15B, 15C and 15D are cross-sectional views similar to FIG. 15 but showing alternative embodiments for the dual lumens in the aspiration needle.

FIG. 16 is a side elevational view partially in cross-section of another embodiment of the present invention.

FIG. 17 is a side elevational view of a distal extremity of a needle incorporating another embodiment of an aspiration needle of the present invention.

Figure 7:
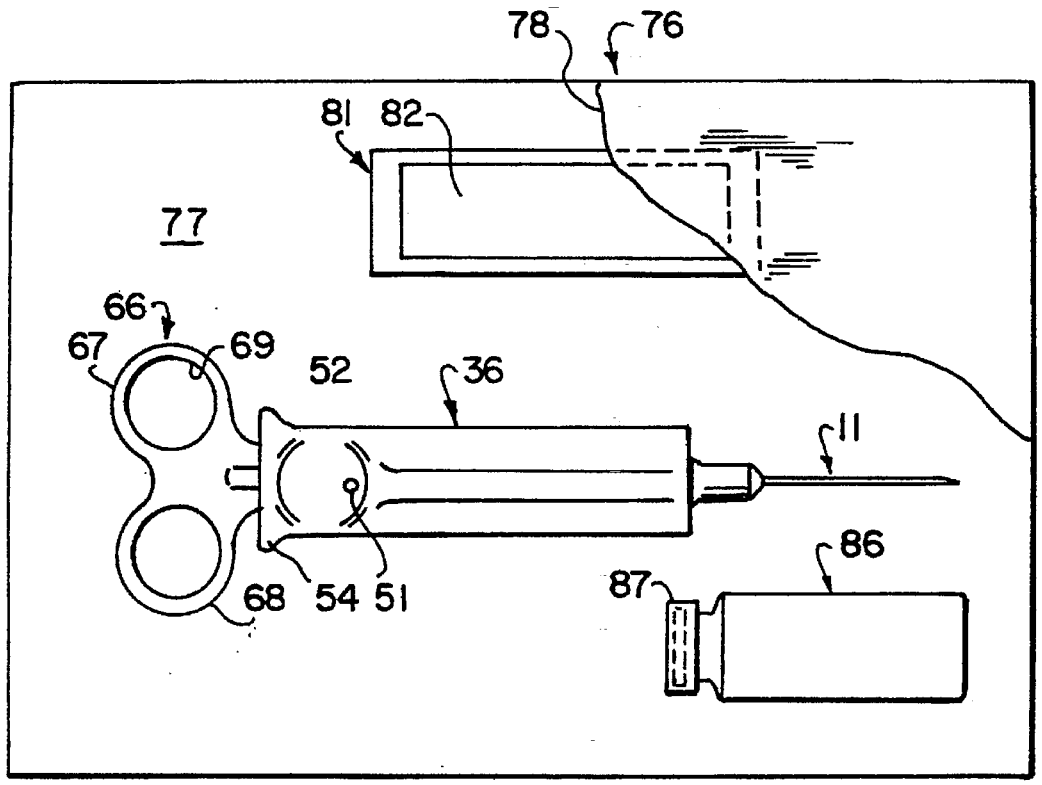
FIG. 7 is a plan view of a kit incorporating the present invention.

In general, the aspiration needle incorporating the present invention for use with a syringe for fine needle aspiration cytology is comprised of a rigid elongate tubular member having distal and proximal extremities. The distal extremity is formed to provide a sharp point. The tubular member has a bore extending therethrough from the distal extremity to the proximal extremity. A body is secured to the proximal extremity of the tubular member and forms a chamber which is in communication with the bore of the tubular member. The chamber is formed by a sloping continuous uninterrupted side wall leading to the bore of the tubular member. The body secured to the proximal extremity of the tubular member includes means for receiving the syringe and for establishing communication between the syringe and the chamber.

More particularly, the aspiration needle 11 which is shown in FIGS. 1 and 2 consists of a rigid elongate tubular member 12 formed of a suitable material such as stainless steel. The tubular member 12 should have a suitable length so that it can reach tumors as hereinafter described. Typically the tubular member should have a length ranging from 2 to 8 centimeters. The tubular member can have an external diameter corresponding to the size of a 23 gage needle. For example it can have an outside diameter of approximately 0.025 inches with an inside diameter ranging from 0.018–0.020 inches to provide a wall thickness ranging from 0.0025 inches to 0.003 inches to provide the desired column strength for the needle. The tubular member 12 is provided with distal and proximal extremities 13 and 14. The distal extremity 13 is formed to provide a point, as for example by sharpening the same in the form of an inclined wedge as shown in FIG. 1. The tubular member is provided with a bore 16 which extends from the distal extremity 13 to the proximal extremity 14. As shown in FIG. 1, the proximal extremity 14 of the tubular member 12 can be flared outwardly to provide a funnel-shaped recess 17 leading into the bore 16. It has been found that by providing a tubular member having such a wall thickness it is still possible to achieve the necessary column strength for the tubular member so that the needle can be introduced into the tissue that it is desired to penetrate.

A body 21 formed of a suitable transparent material such as ULTEM is mounted on the proximal extremity 14. The body 21 by way of example can be formed in two parts 21a and 21b which are joined together at a joint 22 formed by cooperating annular recesses and flanges joined together by suitable means such as ultrasonic bonding. The body 21 can have a generally cylindrical configuration and has formed therein a chamber 26 which is shown as being generally spherical which is in communication with the funnel-shaped passage 17 and the bore 16. The chamber 26 is formed by a wall of the body that has a highly polished surface and is sloping and uninterrupted leading into the funnel-shaped passage 17 and provides a smooth transition with no interruptions between the wall forming the chamber 26 and the flanged proximal extremity 14 of the tubular member 12.

The chamber 26 can be of a suitable size, as for example from 0.075 milliliters to 0.15 milliliters and preferably approximately 0.1 milliliters. As can be seen, the joint 22 extends across the chamber 26 to permit ready access to the chamber so that the tubular member 12 with its swaged proximal extremity 14 can be readily mounted in the part 21a. This also makes it possible to ensure that there are highly polished surfaces in the chamber and that there is an uninterrupted sloping wall leading into the funnel-shaped passage 17.

The part 21b of the body 21 serves as a hub and has a tapered circular recess 31 which is adapted to receive a conventional syringe or a syringe 36 incorporating the present invention of the type shown in FIGS. 3–6. The body 21 is provided with a small bore 37 offset to one side of the recess 31 which extends from the tapered recess 31 into the chamber 26.

The syringe 36 consists of a barrel 41 formed of a suitable material such as plastic. As shown, it is generally cylindrical in shape and is provided with an inner cylindrical recess or chamber 42 which is in communication with a bore 43 provided in a tubular extension 44 of the barrel 41. The barrel 41 is provided with an elongate protrusion 46 formed integral therewith which extends longitudinally of the barrel 41 and has a bore 47 extending along the length thereof with the distal extremity being in communication with a hole 49 entering into the cylindrical chamber 42. The proximal extremity of the bore 47 opens through a hole 51 which is disposed in the distal extremity of a finger-shaped recess 52 provided in the barrel near the proximal extremity of the barrel 41 for grasping by the middle finger. A thumb-shaped recess 53 is also formed in the barrel 41 generally opposite the recess 52. The proximal extremity of the barrel 41 is provided with an outwardly extending annular lip 53 which is adjacent the recesses 52 and 53.

The syringe 36 also includes a plunger 56 which is slidably mounted within the chamber 42 and consists of a cross-shaped member 57 (see FIG. 4) having first and second radially extending flanges 58 and 59 provided on the distal extremity of the plunger 86 to form an annular recess 61 in which an o-ring 62 is disposed. A handle 66 is provided on the proximal extremity of the plunger 56 and is formed integral therewith and consists of a pair of finger rings 67 and 68 which lie in a plane and which are disposed adjacent to each other. The rings 67 and 68 are provided with finger-sizes openings 69 through which the fingers of the human hand can extend.

Operation and use of the aspiration needle 11 and the syringe 36 can now be briefly described as follows. Let it now be assumed that it is desired to perform a fine needle aspiration cytodiagnosis to provide an accurate nonsurgical diagnosis of a lump which has been found by palpation or other means in a human body such as in a female breast. Let it also be assumed that the surgeon has available an aspiration needle 11 and a syringe 36 incorporating the present invention which has been incorporated into a kit such as shown in FIG. 7 which can be in the form of a blister pack 76 in the form of a cardboard back 77 with an overlying transparent plastic wrap 78. In the blister pack 76 in addition to the syringe 36 and the aspiration needle 11 there is provided a slide carrier or holder 81 which contains a plurality of prepared glass slides 82 of a conventional type, as for example two or three slides which may have been coated with lysine in preparation for dry smears.

Also enclosed in the kit 76 is a bottle or vial 86 which is provided with a cap 87 having a central portion 88 of a conventional type which can be penetrated by the aspiration needle 11. An appropriate chemically defined medium (not shown) is disposed within the hermetically sealed bottle or vial 86 in the form of a liquid with a gaseous atmosphere overlying the liquid. The gaseous atmosphere can be of various types, as for example it can be 100% oxygen to facilitate viability of cancer cells in the medium during transportation of vial 86 to a laboratory.

The surgeon would open such a kit 76 and take out the sterile syringe 36 with the aspiration needle 11 attached thereto and take one of his hands and place the thumb of that hand in the recess 53 and another finger of the hand, as for example the middle finger in the recess 52 and at the same time closing the hole 51. Two other fingers of the same hand as for example the index finger and the ring finger would then be inserted through the finger holes 69. The surgeon using the other hand would locate the palpable breast tumor with the other hand and then would use the hand holding the syringe to introduce the fine aspiration needle 11 through the skin and would direct the needle into the palpable tumor. As soon as it has been assured that the needle has penetrated the tumor, a negative pressure or vacuum can be created within the syringe to aspirate cells and fluid from within the tumor. This can be readily accomplished by the surgeon by withdrawing the plunger 56 with two fingers of the hand while holding a thumb and forefinger in the recesses 52 and 53 to keep the hole 51 closed with the finger to create a subambient condition within the chamber 42 to cause aspirate to be drawn into the bore 16 and the chamber 26 of the needle 11. Since the bore 37 has been offset to one side of the recess 31, there is much less likelihood that aspirate coming through the bore 16 will enter the passage 37 but will all be retained in the bore 16 and the chamber 26.

After the desired amount of aspirate has been withdrawn from the tumor as determined by viewing the presence of aspirate in the chamber 26, the needle 11 can be withdrawn. As soon as the needle 11 has been withdrawn and its distal extremity is exposed to ambient atmospheric pressure, the finger disposed in the recess 52 can be lifted to open the hole 51. Two fingers of the hand can then be utilized to further retract the plunger 56 to draw air into the chamber 42. As soon as sufficient air has been drawn into the chamber 42, the hole 51 is again closed by the middle finger with the middle finger and the thumb grasping the barrel 41 and the index and ring fingers engaging the handle 66 to discharge the air which has been drawn into the chamber 42 to be discharged through the needle 11 to force the aspirate in the chamber 26 and the bore 16. This aspirate can be discharged onto the slides 82 after they have been removed from the slide holder 81. After the aspirate has been discharged onto the slides 82, the slides 82 can be wiped together to form smears on the slides. They can thereafter be air dried and shipped to the laboratory for analysis.

During the same aspiration procedure, a portion of the aspirate or if desired all of the aspirate which has been removed from the tumor can be injected into the medium contained in the hermetically sealed vial 86 by introducing the needle 11 through a central needle penetratable portion 88 provided in the cap 87 and discharging the aspirate into the medium. The syringe can then be withdrawn and the vial 86 can be shipped to the laboratory.

Thus, with such procedures it is possible to prepare slides 82 and the vial 86 so that they carry aspirate for diagnosis by the laboratory. With the syringe 36 hereinbefore described with its air vent, the syringe 36 can be closed off by a finger of the hand. This makes it possible to hold the syringe 36 during the aspiration procedure in a way that retains a sensitivity of feeling where the needle is going while at the same time making it easy to seal off the air vent. Also by providing the air vent in the barrel in the syringe, it is possible to introduce air into the cylindrical chamber 42 without the necessity of separating the syringe 36 from the aspiration needle 11 to thereby readily facilitate the expulsion of the aspirated cells and fluid from the needle 11 onto the slides 82 or into the vial 86.

Typically, a surgeon would utilize the middle finger and the thumb for grasping the barrel by placing the middle finger in the recess 52 and the thumb in the recess 53 and utilizing the index finger and the ring finger for pulling the plunger 56 rearwardly or back. It should be appreciated that if desired, it is possible to provide a plunger with only a handle which can be engaged by a single finger of the hand rather than a handle which permits the use of two fingers of the hand.

The use of the aspiration needle 11 of the present invention is particularly advantageous in that its reduced wall thickness permits larger samples to be obtained with a fine needle no greater in size than those heretofore utilized. Thus sample sizes ranging from 10,000–100,000 cells with a volume of fluid ranging from about 0.05 milliliters to about 0.5 milliliters can be obtained. The provision of the visible chamber 26 ensures that it is possible to obtain adequate samples. Chamber 26 as hereinbefore described is formed in such a manner so as to have very smooth inner surfaces and to have sloping uninterrupted walls so that aspirate cannot be entrapped in the chamber and therefore can be readily expelled from the needle.

Although the use of the aspiration needle 11 and the syringe 36 have been described primarily in connection with the obtaining of aspiration samples from breast tumors, it should be appreciated that the aspiration needle 11 and the syringe 36 can be utilized for obtaining samples from other organs of the human body. For example, such a needle can be utilized for obtaining aspiration samples from the liver. In such a case, the length of the needle should be increased to about 6–8 centimeters with appropriate changes in wall thickness to provide adequate column strength. The aspiration needle has been kept as fine as possible, in other words the small diameter is possible in order to cause as little trauma to the tumor being analyzed as well as little discomfort to the patient as possible. At the same time it is desirable to obtain as large a specimen as possible in such a fine needle by providing a maximum internal diameter within the needle while still maintaining the necessary column strength for the needle to minimize bending or collapse of the needle during the aspiration procedure. By utilizing such a fine needle, it is possible to prevent bleeding and damage around the tumor without disturbing the integrity of the tumor.

Figure 8:
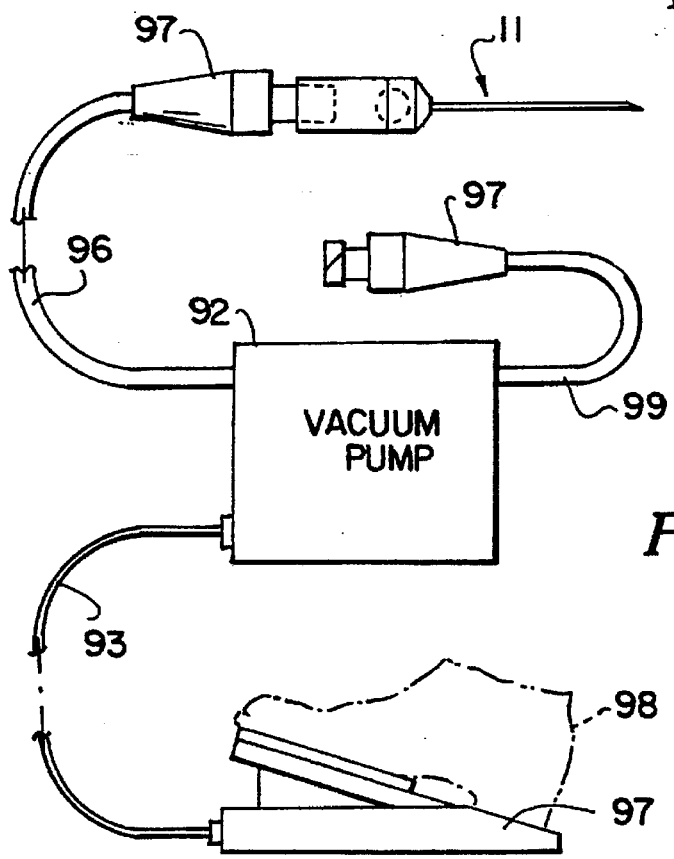
FIG. 8 is a schematic illustration of a foot-operated apparatus incorporating the present invention for use in fine needle aspiration cytology.

Apparatus 91 for utilizing the aspiration needle 11 of the present invention is shown in FIG. 8 and consists of a conventional vacuum pump 92. The vacuum pump 92 can be operated in a suitable manner such as by electric motor (not shown) which is connected by a cord 93 to a foot operated pedal 94 for supplying a subatmospheric or a vacuum condition to a tube 96 which is connected to a fitting 97 that is adapted to be releasably mounted in the tapered recess 31 provided in the needle 11. It should be appreciated that the desired vacuum can also be created by mechanical motion utilizing a foot-operated pump.

Operation and use of the apparatus shown in FIG. 8 may be briefly described as follows. Typically it may be desirable to utilize the apparatus shown in FIG. 8 when it is desired to do aspiration cytology under ultrasonic control making it desirable to utilize the other hand for holding the sonic source. For some operators, the suction pump technique may be preferable to use of a syringe for obtaining adequate aspiration specimens. The foot 98 of the surgeon can then be utilized for operating the foot pedal 94 to supply a vacuum to the aspiration needle 11 at the appropriate time. After the needle 11 has been withdrawn, the vacuum pump 92 can be provided with a control (not shown) which can reverse the vacuum in other words to supply air under pressure through the tube 96 to discharge the aspirate in the needle 11 onto slides 82 or into a vial 86 as hereinbefore described. This would require a 'fail safe' mechanism (not shown) to prevent injection of air into the patients. Alternatively, the vacuum pump 92 can be provided with two tubes, one tube 96 as hereinbefore described supplying a vacuum and the other tube 99 supplying air under pressure. A fail safe device to prevent air under pressure being injected into the patient could be achieved by making the tube 99 too short to reach the patient. Tube 96 having the vacuum would be utilized to withdraw aspirate and the other tube 99 with a similar fitting 97 would be used to discharge the aspirate from the needle 11. A fail safe device would be required to prevent such pressure from being exerted while the aspiration needle is in the patient.

Another embodiment of an apparatus 101 incorporating the present invention is shown in FIG. 9. As shown therein, it is very similar to that shown in FIG. 8 with the exception that a pump with a pulsating vacuum 102 is provided in place of the vacuum pump 92. Such pumps for creating a subatmospheric pulsating vacuum are well known to those skilled in the art. For example, see U.S. Pat. No. 2,918,917 which discloses an apparatus for producing a negative pressure by use of a vibrating device which utilizes a movable diaphragm. Since such pumps are well known to those skilled in the art, it will not be described in detail. It is desired that the pump produce pulse-like wave form 106 such as shown in FIG. 10 in which the amplitude and frequency of the pulses can be varied or adjusted. Thus, as shown, there can be provided low amplitude pulses 107 which commence at 0.1 atmosphere and go to 0.4 atmosphere followed by high amplitude pulses 108 which start at 0.1 atmosphere and go to 0.8 atmosphere as shown in FIG. 10, with the repetition rate for the lower amplitude pulses 107 being at 10 per second and the repetition rate for the higher amplitude pulses 108 being at 5 per second. However, it should be appreciated that in accordance with the present invention various frequencies and amplitudes can be utilized for the pulses The use of such a pulsating vacuum is desirable because it will create mechanical motion of the cells being aspirated. This pulsating vacuum will be transmitted all the way through the needle 11 to the tip and into the tumor and help to dislodge cells and thereby facilitate cells being sucked from the tumor into the needle 11 and into the chamber of the needle 11.

In FIG. 11 there is shown another embodiment of the apparatus of the present invention in which it is possible to achieve mechanical motion of a needle 111 similar to the needle 11. Rather than applying mechanical motion to the cells by a pulsating vacuum as shown in FIG. 9, the needle 111 is vibrated mechanically. This is accomplished by providing a ring 113 formed of a suitable ferromagnetic material such a silicon iron which is secured to the hub 112b of the body 112 having two parts 112a and 112b by suitable means such as an adhesive (not shown). Alternatively, the ring 113 can be applied by a friction fit to the hub 112b. As shown in FIG. 11, the needle 111 with a syringe 36 mounted thereon is adapted to carry an annular electromagnetic coil 116 which is connected to a power supply 117 by leads 118 for supplying a pulsed electrical energy thereto. The coil 116 is disposed between annular pole pieces 119 and 121 formed of a ferromagnetic material forming an annular air gap 112 therebetween just distal of the ring 113. The pole pieces 119 and 121 are supported on the hub 112b by a housing 123 formed of a suitable insulating material, such as plastic. The housing 123 is provided with an inwardly and radially extending annular yieldable member 124 that is L-shaped in cross-section. The innermost portion of the member 123 defines a hole 126 and is seated in an annular recess 127 provided in the outer surface of the body 112 and yieldably urges the pole pieces 119 and 121 to attempt to decrease the spacing in the air gap 122. The electrical signal from the power supply 112 can be in the form of an AC signal which can be varied in amplitude and frequency to create longitudinal movement of the needle 111 along the longitudinal axis of the coil 116 against the yieldable force provided by the member 124. Thus, the pulsating magnetic field created by the coil 116 is translated into longitudinal mechanical motion of the needle 111 to cause the tip of the needle 111 to vibrate in range from a few tenths of a millimeter to several hundred microns. This mechanical motion of the needle should make it easier for the needle to penetrate the skin during the time the needle is being introduced to enter into the tumor. After the tip of the needle 111 is disposed in the tumor, the mechanical vibration of the needle encourages cells to dislodge and become aspirated through the lumen 16 and into the chamber 26 of the needle. In such embodiment, the needle 11 can be vibrated at a frequency ranging from 10 Hertz to 10,000 Hertz.

In FIG. 13, there is shown another embodiment of an apparatus incorporating the invention, which can be utilized with the power supply 117 shown in FIG. 11. It includes a needle 111 of the type hereinbefore described. However, in this case, rather than the ferromagnetic tube or ring 113 being disposed outside on the hub of the needle 111, a ferromagnetic tube or ring 128 is shown embedded within the hub and can be incorporated into the hub during injection molding of the hub. It should be appreciated that the ring 128, rather than being a ferromagnetic ring, can be in the form of a circular magnet or, alternatively, a plurality of separate magnets (not shown) circumferentially disposed within the hub. The coil 116 can be supplied with pulsating power from the power supply 117 of the type hereinbefore described to cause the needle to be mechanically vibrated in the same manner as the needle 111 shown in FIG. 11.

Another embodiment of an aspiration needle 131 incorporating the present invention is shown in FIGS. 14 and 15. The aspiration needle 131 consists of a tubular member 132 having proximal and distal extremities 133 and 134. It is provided with first and second lumens 136 and 137 extending from the distal extremity 134 to the proximal extremity 133. As shown particularly in FIG. 15, the lumen 136 has a diameter which is substantially greater than that of the lumen 137 for a purpose hereinafter described. The distal extremity 134 of the tubular member 132 is provided with a taper 141 to provide a sharpened end for the needle. The distal extremity of the smaller lumen 137 is closed by a plug 142 so that fluid passing in the lumen 137 must pass through a side opening 143 provided in the sidewall of the tubular member 132 and is spaced from the opening 144 provided for the passage 136 at the distal extremity 134 of the needle 131.

The proximal extremity 133 of the aspiration needle 133 can be mounted in a body 146 serving as a hub of a suitable plastic such as polycarbonate in the same manner as shown for the aspiration needle shown in FIG. 1. The body 146 is formed of two parts 146a and 146b, which can be bonded together in a suitable manner such as by an adhesive or ultrasonic welding. The large passage or lumen 136 opens into a generally spherical cavity 151 provided within the body 146 which opens into a passage 152. The passage 152 opens into one side of a tapered recess 153 which is circular in cross-section that is adapted to receive a fitting (not shown) connected to a vacuum source or to a pulsating vacuum source as shown. The smaller lumen 137 in the tubular member 132 is in communication with a passage 156 provided in the body 146 and which is in communication with a tapered recess 157 which is also circular in cross-section. The recess 157 is adapted to receive a fitting (not shown) which can be connected to a source of fluid, as for example a saline solution under pressure.

Use of the aspiration needle as shown in FIGS. 14 and 15 is similar to that hereinbefore described. However, when the needle has been introduced into the tumor, the surgeon accomplishing the procedure could inject a small amount of saline solution by causing a saline pump (not shown) to introduce the saline solution through the passage 156 and into the lumen 137 and out through the side port or opening 143 into a tumor. The saline solution enters the tumor and washes away cells from the tumor so that they can be more readily withdrawn into the opening 144 into the passage 136 to which there is being applied a vacuum or pulsating vacuum to cause those cells to pass through the lumen 136 into the collection chamber or cavity 151. In the construction shown, it can be seen that the smaller lumen 137 is closed at the tip and the saline solution must exit through this side making it necessary for the saline solution to traverse tissue in the tumor to aid in dislodging cells from the tumor before the saline solution is picked up an aspirated through the larger lumen 136 and collected in the cell chamber 151. The spacing between the side opening 143 and the end opening 144 ensures that the saline solution must pass over at least some of the surface of the tumor to help to dislodge cells for aspiration into the cell chamber.

It should be appreciated that with the construction shown in FIG. 15A that the large lumen 136 could be in the form of a coaxial construction in which a tubular member 161 could be in the form of stainless steel providing a larger coaxial lumen 162 with a smaller tubular member 163 of plastic or metal and being disposed coaxially within the lumen 162. It can be provided with a smaller lumen 164 through which the saline solution can be introduced.

In another embodiment as shown in FIG. 15B, a tubular member 166 of stainless steel is provided with a lumen 167 which has disposed therein a tubular insert 168 of a suitable material such as plastic which is provided with a large crescent-shaped lumen 169 and a smaller lumen 171.

Still another embodiment is shown in FIG. 15C in which the tubular member 176 with the lumen disposed therein has a tubular insert 178 of a suitable material such as plastic disposed within lumen 177. The tubular insert 176 is provided with a large centrally disposed, crescent-shaped lumen 179 and a smaller "U"-shaped recess 181 formed in its outer surface extending longitudinally thereof to provide a lumen portion 177A in communication with the lumen 177. Such an arrangement would be advantageous in that it would be easy to form a side opening in the needle to expose the lumen portion 177A to the exterior of the needle mainly by grinding an opening into the sidewall of the needle.

Still another arrangement is possible as shown in FIG. 15D in which a stainless steel tubular member 186 has a "D"-shaped plastic insert 187 which forms a large "D"-shaped passage 188 and a smaller "D"-shaped passage 189 within insert 187 between the tubular insert 187 and the tubular member 186.

From the foregoing it can be seen that a number of different arrangement can be utilized to achieve two lumens in an aspiration needle for the purpose hereinbefore described.

Another embodiment of an aspiration needle 191 incorporating the present invention is shown in FIG. 16, and consists of a tubular member or cannula 192 formed of stainless steel constructed in much the same manner as the tubular member 132 in FIG. 14. It is provided with a large lumen 193 which has an opening 194 at the distal extremity and a small lumen 196 which has a side opening 197. A body 201 is mounted on the proximal extremity of the tubular member 192 and is formed in the manner hereinbefore described. The body 201 serves as a hub and is provided with a relatively large cell collection chamber 202 which is in communication with the large lumen 193 by a passage 203. A passage 204 is provided for establishing connection between the cell collection chamber 202 and a tapered recess 206 which is circular in cross-section and is adapted to be connected to a source of vacuum as shown. A second chamber cavity 207 is provided within the body 201 and has a suitable volume, as for example 1 mm. The body 207 is in communication with the small lumen 196 through a passage 208. A small air vent 209 establishes a communication between the chamber 207 and the outside ambient atmosphere.

In utilizing the aspiration needle 191 as shown in FIG. 16, the chamber 207 would be pre-filled with a desired media, as for example a saline solution. The chamber 207 can be filled by introducing the needle 191 through the rubber cap of a sealed bottle containing the saline solution and with the tip immersed in the saline solution, applying pressure by means of a syringe connected to the cell collection chamber 151. The saline solution will pass through the side opening 197 to fill the chamber 207 permitting air therein to exit through the air vent 209.

After the needle has been introduced into the tumor in the manner hereinbefore described, a vacuum is applied to the needle and a vacuum condition is created at the distal extremity of the tubular member 192. This vacuum condition created at the distal extremity of the tubular member 192 would cause a vacuum to be created in the opening 197 to cause the media or saline solution disposed within the chamber 207 to ooze out of the opening 197 to provide a small amount of saline solution for irrigating and flushing out cells from the tumor so that they can be aspirated through the lumen 193 into the collection chamber 202. The saline solution within the chamber 207 can escape because air can enter through the air vent 209. With the hub or body 201 being transparent, the physician can readily observe as the saline solution within the chamber 207 is being drawn into the tumor and is aspirated along with the cells in the tumor back into the collection chamber 202.

Still another embodiment of an aspiration needle incorporating the present invention is shown in FIG. 17 in which only the distal extremity of an aspiration needle 211 is shown. The tubular member or cannula 212 of this aspiration needle 211 is provided with a large lumen 213 which opens through a side opening 214 proximal of the distal extremity of the tubular member 212. Similarly, the smaller lumen 216 opens through a side opening 217. Since side openings 214 and 217 have been utilized for both the large and small lumens 213 and 216, the distal extremity of the tubular member can be closed, as for example to provide a generally conically shaped end 221. By providing such a conical tip on the distal extremity of the aspiration needle 211, it is possible to avoid damage to the blood vessels in the tumor, thereby substantially reducing the amount of trauma induced into the tumor. The irrigation functions as well as the aspiration functions to collect cells can be accomplished in a manner similar to that hereinbefore described in conjunction with the aspiration needles hereinbefore disclosed.

In connection with the various embodiments of the aspiration needles herein disclosed, it should be appreciated that all of the embodiments of the needle can either have a pulsating vacuum applied to them and at the same time or alternatively be supplied with mechanical vibration to aid in collection of cells from the tumor.

In order to optimize the collection of cells with the aspiration needle and apparatus of the present invention, it has been found that it is desirable to provide as smooth a finish as possible to the surfaces of the needle forming the lumens through which the cells being collected are to pass. By providing smoothly polished surfaces for the lumens, damage to cells when they are being collected is reduced. Such improved surface finishes for the lumens can be achieved by grinding, such as by spinning a diamond burr wheel at high speed to polish the inside surface forming the lumen. Alternatively, the surfaces can be chemically etched to achieve a polished surface. Also it should be appreciated that a coating such as a polymer can be applied on the interior surfaces forming the lumens to provide a slippery, low-resistance surface which is friendly to the membranes of the cells as they are being collected.

From the foregoing it can be seen that there has been provided an aspiration needle and a syringe and apparatus associated therewith and a kit all of which are user friendly and can be utilized for withdrawing relatively large samples of aspirate while retaining the desirable characteristics of fine needle aspiration cytology to minimize disturbance of the tumor and trauma to the patient.

What is claimed is:

1. Apparatus for use by an operator in fine needle aspiration cytology for collecting cells from tissue in a living body to provide a sample comprising a fine aspiration needle having proximal and distal extremities, cell visualization means carried in alignment with the proximal extremity of the fine needle and permitting the operator to see the cells as the cells are being collected, a subambient vacuum source remote from the needle and having an outlet, tubing connecting the outlet of the vacuum source to the proximal extremity of the needle and foot-operated means for controlling the supply of a vacuum from the vacuum source to the needle to thereby control the aspiration of cells from the tissue through the needle while the collection of cells for the sample is taking place and while the visualization means is being viewed by the operator.

2. Apparatus as in claim 1 wherein said vacuum source includes means for supplying a gas under pressure to the tubing connected to the needle.

3. Apparatus as in claim 1 wherein said vacuum source includes means for producing a subambient vacuum in the form of pulsations at the outlet of the vacuum source to provide a pulse-like waveform having a variable amplitude and frequency to create mechanical motion of the cells as they are being aspirated into the needle.

4. Apparatus for use in fine needle aspiration cytology for collecting cells from tissue in a living body comprising a fine aspiration needle having a proximal extremity and a distal extremity and a lumen therein extending from the proximal extremity to the distal extremity, said lumen including a cell collection chamber disposed in the proximal extremity, a vacuum source remote from the fine aspiration needle and having an outlet and including means at the vacuum source for producing a subambient pulsating vacuum to provide a pulse-like waveform having a variable amplitude and frequency at the outlet and means including flexible elongate tubing connecting the outlet of the vacuum source to the proximal extremity of the fine aspiration needle so that the pulsating vacuum is supplied to the lumen in the aspiration needle to create mechanical motion of the cells being aspirated.

* * * * *